Figure 1:
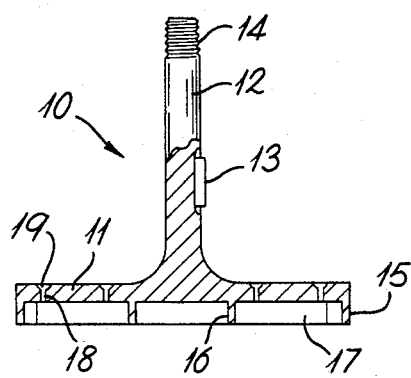

United States Patent [19]

Field

[11] Patent Number: 4,532,660
[45] Date of Patent: Aug. 6, 1985

[54] ENDOPROSTHETIC BONE JOINT DEVICES

[75] Inventor: Richard E. Field, Near Masham, England

[73] Assignee: National Research Development Corporation, London, England

[21] Appl. No.: 495,553

[22] Filed: May 17, 1983

[30] Foreign Application Priority Data

May 17, 1982 [GB] United Kingdom ............... 8214347

[51] Int. Cl.³ .............................................. A61F 1/00
[52] U.S. Cl. .................................. 623/18; 128/92 C; 128/92 CA; 623/23
[58] Field of Search ............. 128/92 C, 92 CA, 92 B, 128/92 BA, 92 BB; 3/1.91, 1.912, 1.913, 1.911

[56] References Cited

U.S. PATENT DOCUMENTS

| | | | |
|---|---|---|---|
| 2,668,531 | 2/1954 | Haboush | 128/92 CA |
| 4,021,864 | 5/1977 | Waugh | 128/92 C X |
| 4,129,903 | 12/1978 | Huggler | 128/92 BB X |

FOREIGN PATENT DOCUMENTS

| | | | |
|---|---|---|---|
| 2305333 | 2/1973 | Fed. Rep. of Germany | 3/1.912 |
| 2603456 | 8/1977 | Fed. Rep. of Germany | 3/1.9 |
| 2478462 | 9/1981 | France | 3/1.91 |
| 1389427 | 4/1975 | United Kingdom | 128/92 BA |
| 0483980 | 10/1977 | U.S.S.R. | 3/1.912 |

Primary Examiner—Richard J. Apley
Assistant Examiner—David J. Isabella
Attorney, Agent, or Firm—Cushman, Darby & Cushman

[57] ABSTRACT

An endoprosthetic bone joint device is secured by filamentary elements driven therethrough into penetrating engagement with bone. These elements will normally exhibit transverse flexibility; they preferably have elastic modulus similar to bone; they can be roughened or barbed for added securement; they can carry material of negative electrochemical potential relative to other parts of the device to induce bone growth intimately therewith; and they can carry material otherwise beneficial to bone growth. The device preferably also has a radiating multi-directional flange formation to engage a corresponding formation cut in the bone.

12 Claims, 4 Drawing Figures

ENDOPROSTHETIC BONE JOINT DEVICES

This invention concerns endoprosthetic bone joint devices and relates more particularly to the securement of such devices to bone, especially, but not exclusively, to one end of a long bone.

Various techniques for such securement have been proposed but those currently established in routine usage commonly involve the penetration into cancellous bone by elongate rigid members of significant size relative to the bone and as a proportion of the overall device.

In the most common of these techniques an elongate member is located as a clearance fit in a pre-prepared site and is secured by the use of a gap-filling medium such as an acrylic cement. While generally satisfactory in many instances, this technique can be problematical if any movement occurs at either of the two interfaces which exist between the gap-filling medium on the one hand and the member and the bone on the other hand. Moreover, such movement can occur as a natural consequence of the differing properties which in practice inevitably occur between the materials of the member, the medium and the bone, particularly as bone is a living material having properties which vary in an individual patient and from one to another. This technique has been improved in recent years by an emphasis on site preparation involving very thorough cleansing followed by pressurized application of the gap-filling medium to enhance the penetration thereof into the bone, but difficulty can still occur.

Another technique seeks to effect improvement by the use of a member having a porous coating or equivalent formation which affords securement not by way of a gap-filling medium but instead by the inward growth of natural fibrous material which ossifies within the member. This can be viewed as problematical by virtue of the inevitable initial period of significant length during which the device is relatively insecure and the patient must be at least partially immobilised. Moreover, longer term difficulty can arise by resorption of ossified in-grown material as a result of differential properties between this material and that of the member.

In yet another technique a member is secured by a tapered interference fit in the bone. A difficulty in this case is that either the fit is localised over only a part of the member such that movement can develop due to the forces acting on the device during subsequent use, or the fit is sufficiently extensive that the initial penetration involves a risk of undue damage to the bone. Again, differential material properties can cause difficulty.

It should be understood that these comments on particular techniques for securement to bone are by no means exhaustive but are intended to provide a brief and somewhat generalised appreciation of the difficulties of a complex situation. However, it will be evident that a common cause of difficulty arises from the largely inevitable use of materials having different properties from bone, and such a difficulty is heightened in its consequences by use of those materials for penetration in relatively bulky form. Moreover, such penetration can be problematical in other ways. For example, the very nature of the penetration is such that any introduced infection will be deeply sited. Also, such penetration can require the removal of a significant volume of bone during site preparation and this is doubly disadvantageous in the consequent reduction of blood flow and in compromising the availability of remedial measures if the associated device is not successful.

It should be mentioned for completeness in this general context that a securement technique does exist in which the above difficulties are notably less evident, but the technique is only commonly applicable to particular situations. The technique in question involves the use of relatively shallow devices having a relieved surface configuration, but no elongate members, for cooperation with a gap-filling medium in a naturally concave site such as the acetabulum of the hip joint. The same technique has been applied to form an effective capping for the femoral head at the hip, but this appears not have been sufficiently successful to have induced a widespread routine usuage due, at least in part, to inadequacy of the resultant anchorage in surviving the forces which act thereon during subsequent usuage of the device.

An object of the present invention is to provide a further technique, and devices therefor, whereby the various difficulties discussed above are reduced. To this end the invention centres in general terms on the provision of a multiplicity of filamentary elements to be driven through part of the device into bone.

Clearly, these elements will not possess, individually or collectively, the relative bulk of the prior penetrating elongate members and this contributes to a reduction in any potentially disadvantageous consequences which can otherwise arise from differential material properties or loss of bone as discussed above. At the same time the elements can penetrate the bone to a significantly greater extent than the prior relatively shallow relieved structures and so afford a more secure anchorage against the effects of the forces which occur in subsequent use of the device. Moreover, this last anchorage can be enhanced by penetration of the elements in a variety of directions to suit an individual situation, whereas the penetration geometry is largely predetermined with the prior devices.

The elements are intended to penetrate the cancellous material of the bone, including the trabecular structure of the medulla. The elements must have sufficient rigidity and other appropriate mechanical properties for this purpose so as to be substantially incompressible relative to the bone material, but the elements will normally exhibit some transverse flexibility to allow bending. Such bending can act to facilitate introduction of the elements, and mutual splaying of the elements resulting from bending will enhance the overall anchorage. Also, a bending capability can potentially accommodate changes in the surrounding bone structure which a bulky rigid material cannot. In this last connection also, the elements are preferably made of a material having an elastic modulus generally similar to that for bone.

The elements are intended to be in direct contact with the bone material without the intervention of gap-filling medium, but the individual contribution of any one element to the overall resultant anchorage can be enhanced in various ways. For example, the elements can be roughened, barbed or otherwise formed to act mechanically against subsequent movement relative to the bone. Also, the elements can be treated or formed to induce or accommodate growth of bone into intimate contact therewith. In one form of the invention for this purpose, the elements are employed covered with or incorporate material such as hydroxyapatite beneficial to bone growth as a substrate, nutrient or protection. In another such form of the invention, the elements are covered with or incorporate a material having negative electrochemical potential with respect to other parts of the device to induce natural growth towards the elements. These two forms of the invention can be combined if the added material gives rise to cathodic dissolution products beneficial to bone growth, or if the cathodic dissolution progressively releases, or exposes for release, additional material incorporated therewith.

In practice the elements can be provided with a uniform length equating with the maximum likely to be needed, with this length being shortened selectively by the surgeon as required in individual situations. Alternatively, a range of lengths can be supplied by the manufacturer.

Also in practice it is appropriate to provide the elements with enlargments at one end for captive locking under compression between two parts of the related device with the free ends of the elements penetrating the bone.

Another preferred feature of the invention is that the part of the device to be located against the bone which the elements penetrate should have a flanged formation projecting therefrom to engage a corresponding slot formation cut in the bone, these formations being multidirectional. More particularly, it is further preferred at present that this formation on the device should comprise flange portions radiating from the central region of the bone-engaging part towards the periphery thereof to transfer shear force loads toward the bone cortex, which last can suitably be embraced by a peripheral annular flange portion.

Figure 2:
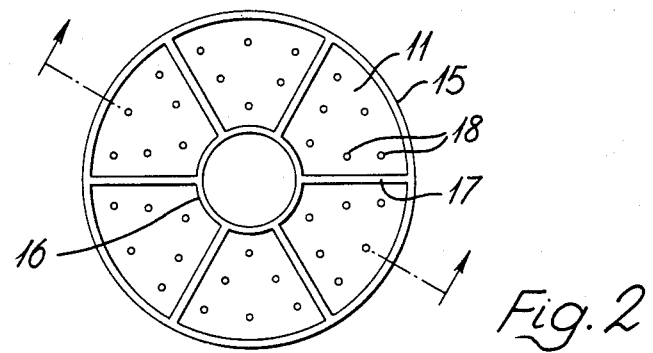
Figure 3:
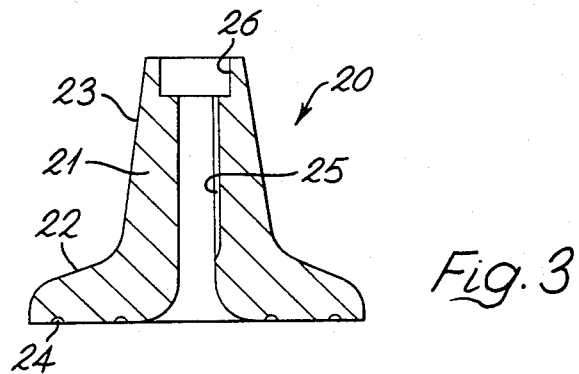
Figure 4:
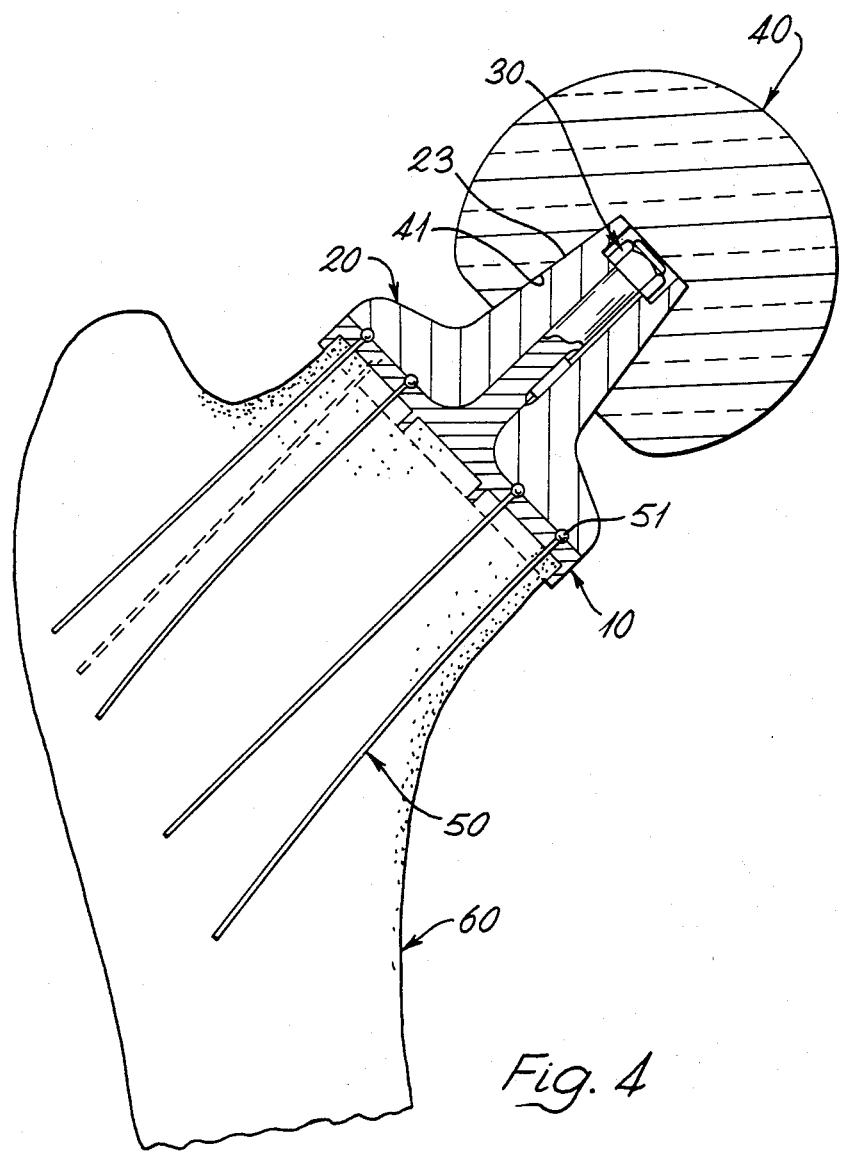

The invention as so far described is clarified, by way of example, with reference to one embodiment thereof illustrated in the accompanying drawings in which:

FIGS. 1 and 2 respectively illustrate one part of the embodiment in partially sectioned side view and inverted plan view, FIG. 3 illustrates in cross-sectional view another such part, and FIG. 4 illustrates these two parts in use with other parts and the associated filamentary elements.

The embodiment of the drawings is a femoral component for use in the hip joint as a hemiarthroplasty in replacement of the natural femoral head, or in that joint as part of a total arthroplasty additionally involving an acetabular component replacing the associated natural pelvic socket in which the head articulates.

The component part in FIG. 1 is denoted 10 and comprises a plate 11 of disc form having a shaft 12 projecting coaxially from one side thereof. This shaft is formed with a key, spline or similar anti-rotation formation at 13 towards its base and is also externally threaded at 14 towards its free end.

On its other side the plate has a flange formation projecting axially therefrom, this formation including a peripherally and concentrially located outer annular skirt 15, a centrally and concentrically located inner annular skirt 16, and a plurality of radially interconnecting webs 17.

Lastly, the part 10 has a plurality of apertures 18 passing axially therethrough between the skirts and webs, each such aperture opening into a hemispherically countersunk recess 19 in the one side of the plate.

The component part of FIG. 3 is denoted 20 and comprises an annular body 21 which converges over its length, which length corresponds to that of shaft 12, through a curved portion 22 at the wider end to a terminal conical taper 23 at the narrow end. The wider end of the body is of corresponding shape to plate 11 and has a plurality of hemispherical recesses 24 corresponding in diameter and distribution to recesses 19. The central passageway of the body is formed with a keyway, spline or other formation at 25 towards the wider end in complementary manner to that at 13 on the shaft 12 to engage non-rotatably thereon with the recesses 19 and 24 superimposed, and the passageway is counterbored at 26 at the narrow end of the body.

FIG. 4 illustrates remaining parts of the component. The parts in question comprise a nut 30 to engage the thread 14 of shaft 12 and seat in the counterbore 26 of body 21, a ball 40 having a conically tapered bore 41 partway therethrough to engage the taper 23 of body 21, and a plurality of filamentary elements 50 sized to pass through apertures 18 and having spherical enlargements 51 at one end complementary with recesses 19 and 23.

Use of the component is also shown by FIG. 4. The femoral head of a femur indicated in partial outline at 60 is excised through the neck to receive component part 10 thereof. The flange formation of this part engages the bone, complementary slots having been cut in the latter to receive the webs 17 and the inner skirt impacting into the upper end of the medulla.

The filamentary elements 50 are then driven through respective apertures 18 into the cancellous bone, the terminal enlargements 51 seating in the recesses 19. The elements are driven in varying directions, suitably to follow the general trabecular pattern in the bone, the elements being selectively sized to avoid emergence through the bone cortex.

Thereafter the component part 20 is engaged over and keyed with the part 10 to seat its recesses 24 over the enlargements 51, this sub-assembly is secured by the nut 30, and the ball 40 is engaged on the part 20 by interference fit between the respective mutually complementary tapers 41 and 23.

The filamentary elements can number between five and thirty, and suitably vary between 3 and 15 cm in length and 0.25 and 2.0 mm in diameter. Regarding materials: the elements are suitably of surface sintered high tensile titanium wire and titanium heads welded thereon, the plate parts 10 and 12 are suitably of a cast chromium-cobalt alloy, the nut can be of similar metal to the plates but with a polyethylene linear to lock the same, and the ball is suitably of a ceramic.

While the invention has just been described with more particular reference to the illustrated embodiment, it is variable in different ways.

Application is, of course, not confined to a femoral component. However this example is apt insofar as such components are the longest established and still most widely used in routine orthopaedic practice involving an endoprosthesis. In addition femoral components in common current usage typify the difficulties first discussed above.

Also, the materials suitable for use with the invention can vary from those indicated for the embodiment and can include other metals, and synthetic and composite materials. Carbon composite material, such as carbon-reinforced carbon fibre form, is thought particularly suitable for the penetrating elements because the elastic modulus can be similar to that for bone and a selected porosity can be provided.

The number and distribution of the penetrating elements can of course be varied to suit individual circumstances. However, it is thought appropriate to concentrate these elements medially and laterally in relation to the femur, these locations being, according to current thinking and understanding, the main load bearing regions within the femur. Moreover, because these regions are considered to be respectively subject to compressive and tensile load forces, the elements may be correspondingly of different forms to better take account of these forces.

The shape of the disc form plate can vary between circular and substantially elliptical to suit the direction of the cut made to excise the femoral head. In nature, apart from differences in overall bone size, the femoral neck has a cross-sectional shape which progresses from circular just below the head to elliptical towards the greater trochanter. Thus provision of a range of shapes as above will be appropriate to suit variation of cut direction by the surgeon and some of this range can be associated with a shaft which is slightly inclined from an axial disposition to allow for a slightly oblique cut. However, it is expected that further development of the invention will determine optimum excision geometry whereby a requirement for undue variation in component geometry is avoided.

A further alternative which may well be found to be preferable is to form the distal surface of the plate, i.e. that surface which is in aposition with the cut surface of the femoral head, as part of a sphere such that all points of contact between plate surface and bone are equidistant from the center of the prosthetic femoral head. Furthermore the radius of the sphere will be equal to the distance between the center of the prosthetic head and the plate to bone interface. By this configuration it is predicted that with the exception of frictional forces arising from the interface between the prosthetic femoral head and the acetabular component, all forces passing through the femoral neck will pass through the plate to bone interface perpendicular to the interface thus minimizing or avoiding shear forces on this interface.

It may also be advantageous to provide a range of separate peripheral skirt members for the proposed femoral component, such members being intended to clip in place. These members will serve to provide a smooth surface to abut with adjacent muscles and other parts of the natural capsule of the hip joint, and offer a choice of depth to suit the requirements of individual patients in this respect.

In yet another variation, the radial flanges can be extended to penetrate the bone further and, in fact, act as the main anchorage for the component. In this case the flanges are, as noted for the filamentary elements, preferably matched to bone in respect of elastic modulus, and additionally formed to promote in-growth. Indeed, these last features can be suitably increased in effect towards the free ends of the flanges.

Lastly, as an indication of the powers of securement afforded by the presently proposed technique: a simplified form of the illustrated embodiment has been made without flanges and secured to the femoral neck of a glycerine embalmed femur with 12 filaments each no longer than 4 cm. This mock-up was tested on an Instron or other compression loading machine at loads of up to 1000 lb without evident deformation either visually or as judged by comparison of pre- and post-stress X-rays.

I claim:

1. An endoprosthetic bone joint device comprising:
a first part defining a support surface to engage a complementery surface of a bone of said joint, said first part having a plurality of longitudinal transverse passageways extending completely through said support surface;
a second part defining an articulation surface for said joint, said second part being connectable with said first part remotely from said support surface;
and a multiplicity of transversely flexible filamentary elements, each said element having a diameter in the range 0.25 to 2.0 mm and a length of at leas 3 cm, and each said element having an enlargement at one end thereof captively located between said first and second parts with the remainder of such element passing through a respective one of said passageways to project from said support surface into said bone thereby anchoring said bone joint device to said complementary surface of said joint.

2. A device according to claim 1 wherein said elements number from five to thirty, and each have a thickness in the range of 0.25 to 2.0 mm and a length in the range 3 to 15 cm.

3. A device according to claim 1 wherein said first part has a flange formation projecting from said surface to a lesser order of distance than said elements, said formation including a plurality of flange portions radiating from a central region of said support surfaces towards the periphery thereof.

4. A device according to claim 3 wherein said flange formation comprises an annular portion extending around the periphery of said support surface.

5. A device according to claim 1 wherein said first and second parts have respective mutually-complementary interface surfaces engaged in the connection of said parts, said first part interface surface having said passageways each formed with a countersunk end and located therein, and said second part interface surface having a plurality of recesses therein superposed with said countersunk ends to locate captively said element enlargements.

6. A device according to claim 1 wherein:
said first part includes a plate form portion having one major face thereof defining said support surface, and an opposed major face from which a shaft projects; and said second part is of two-part construction including a first sub-part of annular form non-rotatably connected around said shaft, and a second sub-part defining said articulatory surface and connected with said first sub-part adjacent the free end of said shaft.

7. A device according to claim 1 wherein said support and articulatory surfaces are each convexly spherically shaped on a common spherical center.

8. A device according to claim 1 wherein each said element has a roughened surface to act against removal when penetrated into bone.

9. A device according to claim 1 wherein each said element carries a material active as a bone growth medium in intimate contact with bone.

10. A device according to claim 1 wherein each said element incorporates material having a negative electrochemical potential with respect to other parts of the device.

11. An endoprosthetic bone joint device comprising:
a first part defining a support surface to engage a complementary surface of a bone of said joint, said first part having a plurality of longitudinal transverse passageways extending completely through said support surface and each said passageway being countersunk at its end remote from said support surface;

a second part defining an articulation surface for said joint, said second part being connected to said first part to cover each said passageway countersunk end;

and a multiplicity of transversely flexible filamentary elements numbering at least five, each said element having a diameter in the range 0.25 to 2.0 mm and a length of at least about 3 cm, and each said element having an enlargement at one end thereof captively located in one of said countersunk passageway end between said first and second parts with the remainder of such element passing through a respective passageway to project from said support surface into said bone thereby anchoring said bone joint device to said complementary surface of said joint.

12. The method of using an endoprosthetic bone joint device, which device comprises:

a base body part defining a support surface;

an outer body part defining an articulatory surface; and a multiplicity of transversely flexible filamentary elements each having an enlargement at one end;

and which method comprises:

shaping the articular end of a bone of said joint to receive said base body part as a close fit by way of said support surface;

locating said base body party in said close fit;

driving said elements, with said enlargements trailing, maximally through said base body part to penetrate said shaped bone while varyingly orientating said elements to follow the general trabecullar pattern in said bone; and thereafter connecting said outer body part with said base body part to locate said element enlargements captively therebetween.

* * * * *